United States Patent [19]
Pickett et al.

[11] 3,982,862
[45] Sept. 28, 1976

[54] TWO-PART COMPOSITE DEVICE FOR HISTOLOGIC TISSUE PROCESSING AND EMBEDDING

[76] Inventors: John E. P. Pickett, 3323 Pinafore Drive; Thomas D. Kinney, 3120 Devon Road; Gene M. Winders, 5332 N. Willowhaven Drive, all of Durham, N.C. 27705

[22] Filed: Jan. 22, 1976

[21] Appl. No.: 651,505

Related U.S. Application Data
[63] Continuation-in-part of Ser. No. 564,595, April 3, 1975, abandoned.

[52] U.S. Cl. .............................. 425/117; 128/2 B; 220/4 F; 249/83
[51] Int. Cl.² ..................... B29C 1/00; B29C 1/14
[58] Field of Search ................... 425/117, 84, 185; 249/470, 83, 160; 128/2 B; 206/45.2; 220/4 C, 4 E, 4 F, 281

[56] References Cited
UNITED STATES PATENTS

| | | | |
|---|---|---|---|
| 1,867,447 | 7/1932 | Dunn | 206/45.2 |
| 3,128,902 | 4/1964 | Barnum | 220/281 |
| 3,411,185 | 11/1968 | Pickett | 425/117 |
| 3,456,300 | 7/1969 | Pickett | 425/117 |
| 3,674,396 | 7/1972 | McCormick | 425/117 |

*Primary Examiner*—Francis S. Husar
*Assistant Examiner*—Carl Rowold
*Attorney, Agent, or Firm*—B. B. Olive

[57] ABSTRACT

A two-part histologic tissue processing and embedding structure comprises an open-ended base pan and a perforated top member. For processing, the base pan and top may be sna-fitted together to form a compact housing for holding and transporting the tissue specimens through the various processing liquids. For embedding, the top is inverted so that the top and base pan may be loosely seated together as a mold for receiving paraffin which solidifies to embed the tissue specimen. For slicing, the base pan is used as a microtome clamp aligning device and is then removed and the top serves a mounting device for mounting the embedded specimen in a microtome clamp during slicing, and for storage the base pan may be secured back onto the top and placed over the remaining unsliced embedded specimen for protection.

12 Claims, 12 Drawing Figures

ETCHED WRITING SURFACE

TWO-PART COMPOSITE DEVICE FOR HISTOLOGIC TISSUE PROCESSING AND EMBEDDING

CROSS-REFERENCE TO RELATED APPLICATION

This application is a continuation-in-part of Ser. No. 564,595, filed Apr. 3, 1975 and now abandoned.

BACKGROUND OF THE INVENTION

1. Field of the Invention

The invention relates to histologic tissue processing and more specifically to composite tissue processing and embedding structures.

2. Description of the Prior Art

The two-part structure taught by U.S. Pat. No. 2,996,762 to James B. McCormick includes an embedding box which is comprised of a boat receptacle and a paraffin housing structure which is adapted to be received by the microtome device. The housing structure is loosely placed or seated on the boat receptacle after the tissue specimen has been positioned in the boat receptacle and the composite structure is filled with liquid paraffin. The boat receptacle is removed from the housing structure after the paraffin has hardened and may be reused or discarded while the housing structure in which the paraffin tissue block remains may be placed in the microtome and have certain sections cut from the same after which the remainder of the paraffin block and the housing structure is catalogued and filed for future reference. The housing structure is provided with internal projections which secure the molded block to the housing and with an external flange which is required for the same to be placed in a microtome device in alignment with the microtome cutting blade. The internal projections interfere with positioning of the specimen and thus it has been the practice to position the tissue specimen in the boat receptacle before seating the housing structure on the boat receptacle.

In order to prepare a tissue specimen to be placed into the embedding structure of McCormick, the tissue specimen must first be exposed to the usual processing liquids such as alcohol, xylene, liquid paraffin, and the like, and which under conventional practice requires a separate type of receptacle for holding the tissue. That is, unlike the two-part structure of the present invention, the McCormick housing and boat elements have no utility as a processing receptacle, and consequently a separate processing structure, such as disclosed in U.S. Pat. No. 3,128,902, is required. The use of separate processing and embedding receptacles necessitates a removal of the tissue specimen from the processing receptacle after processing and a transfer of the tissue to the embedding receptacle.

The above practice was greatly improved by the introduction of the three-part processing and embedding receptacle taught by U.S. Pat. No. 3,456,300. This structure eliminated the need to remove the tissue specimen from the processing receptacle and transfer it to a separate embedding receptacle. However, it has been found that this structure takes up a great deal of space during processing and thus substantially reduces the number of tissue specimens which can be processed in a given cycle. The structure of U.S. Pat. No. 3,456,300 is also more expensive to manufacture and more complicated to use than the present invention.

U.S. Pat. No. Re. 28,165 discloses a three-part processing and embedding device. The device comprises an open-topped, box-like processing pan having a perforate bottom wall, a perforate cover member and an open-topped, box-like base embedding pan. For processing, the tissue specimen is placed in the processing pan and the cover is placed over it to make an integral, perforate processing unit. After processing, the cover is removed and the tissue specimen is lifted out of the processing pan and transferred to the embedding pan. The processing pan is then placed in coupled relation over the embedding pan to form an embedding unit. This patented device teaches the use of the perforate bottom wall of the processing pan as the means for trapping the hardened paraffin body. However, the principal drawbacks of this device are that it requires three parts and its use requires that the specimen be transferred from one pan to another, thereby risking the loss of identity of the specimen and damage to the specimen. No teaching in this patent suggests the design of a two-part receptacle useful for both processing and embedding and which does not require the specimen to be lifted and transferred from one pan to another.

Another three-part structure is taught by U.S. Pat. No. 3,411,185. A further type of three-part receptacle having a telescoping arrangement is taught by allowed copending application Ser. No. 487,463, filed July 11, 1974, and entitled "Compact Telescoping Tissue Processing, Embedding Microtome Holder and Storage Receptacle". This latter type of receptacle uses substantially less space than prior receptacles but does require three parts.

U.S. Pat. No. 1,867,447 to F. J. Dunn teaches a two-part display box made from light wood or fibrous material and adapted for storage and display of articles such as cigars and candy. The box comprises two open-ended, box-like members which join together in a first configuration to form a closed, imperforate box and in a second configuration, with the cover supporting the base, to form a display box for displaying the articles to be vended. This patent does not suggest the use of a similarly constructed box in the tissue processing and embedding art. The Dunn box does not lend itself to the processing and embedding of tissue speciments for a number of reasons. First, the display box would not allow embedding of tissue because it has straight sidewalls. When paraffin hardens, an angled wall is required to allow removal of the hardened paraffin body. Secondly, for processing tissue, a perforated cover is required to allow fluid penetration into the unit and to allow drainage after each processing fluid is introduced into the unit. Third, the bottom surface of the embedding unit must be thin and have heat transfer characteristics which will allow rapid cooling of the tissue when embedding with molten paraffin. Fourth, the materials used in the construction of tissue processing and embedding units must be selected with great care so as to be inert to the harsh fixatives and solvents used in processing. The material must also be capable of withstanding the heat used in melting of the paraffin. The material must be non-absorbent so that it will not absorb the various processing fluids and will not absorb the molten paraffin. An absorbent material would swell during the process and make it impossible for the dimensions of the unit to be retained during the process for proper securement. Furthermore, the material must be sufficiently rigid and sturdy to withstand the pressure from the opposed jaws of a microtome clamp. It is believed, therefore, that the Dunn display box and similar boxs are wholly inadequate to teach, suggest, or make obvious the use of a two-part receptacle for the processing and embedding of histologic tissue specimens.

It can thus be seen that the prior art teaches a two-part device for embedding and subsequent operations and a number of three-part devices which are useful for processing, embedding, slicing and storage. However, with the increasing number of histologic specimens being processed in medical centers throughout the world, there is an acute need for a simple, inexpensive, two-part structure which is useful for all of the operations, i.e., processing, embedding, slicing and storage. Such a structure has not heretofore been available.

SUMMARY OF THE INVENTION

The two-part histologic tissue processing and embedding device of the invention comprises an open-ended, rectangular top member which interconnects with a mating open-ended base pan in two configurations to form both a processing device and an embedding device. The closed end of the top member is a perforate wall whereas the closed end of the base pan is a thin solid wall having only one aperture. A continuous ledge formation is provided on the interior sidewall surfaces of the base pan to maintain the top at a predetermined and precise distance from the closed end of the base pan in both the processing and embedding modes. In the processing mode, the top is snap-fitted into the base pan and serves as a perforate cover for the base pan to house the tissue specimen, and the entire structure provides an integral, perforate enclosure for transporting the tissue speciment through the usual processing. fluids.

The structure is put into an embedding mode by inverting the top and seating it in the base pan so that it rests on the ledge. In the embedding mode the two-part structure serves as a mold for the liquid paraffin which hardens around the tissue specimen and the perforate wall of the inverted top serves to trap the molded paraffin. During slicing, the base pan first serves as a clamp aligning device and is then removed and the top is used as a mount for mounting the embedded specimen in the microtome clamp. After slicing, the base pan can be securely placed over the remaining unsliced embedded specimen for protection during storage. Thus, the two part structure of the invention provides a device which is simple to manufacture and which can be used for processing and embedding as well as for an aligning device preparatory to slicing, as a mount during slicing, and later as a protective device for storage.

DESCRIPTION OF THE PREFERRED EMBODIMENT

Figure 1:
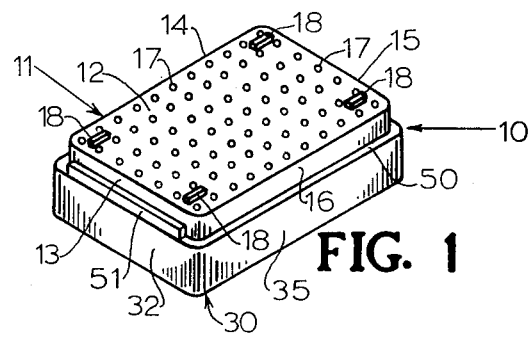
FIG. 1 is a perspective view of the base pan and top member of the invention interconnected to form a processing unit.

The first element of the composite two-part receptacle and embedding structure 10 is a top member 11 which includes a rectangular central wall 12 having openings 17 and perpendicularly extending sides 13, 14, 15 and 16. Sides 13, 14, 15 and 16 are integrally connected to the perforate wall 12 at right angles to form, in combination with wall 12, the open-ended rectangular top 11. As later explained, openings 17 in wall 12 serve as a means for admitting the various processing fluids and hot liquid paraffin into the composite structure 10. Top pan 11 may be molded from a thin resilient plastic such as polypropylene which is inert to the various processing liquids, which is nonabsorbent and which will retain its shape and dimensions during exposure to the processing fluids and the heat of the molten paraffin. In the preferred embodiment, the entire two-part structure has been molded from "Celcon" plastic manufactured by the Celanese Corporation. Top 11 is also preferably provided with a plurality of knobs 18 mounted inwardly of the periphery and which extend outwardly from the outer surface of wall 12 and which provide means for spacing several of the structures 10 from each other when the same are stacked on their sides during the fixation process and which allow the fixation fluids to enter and leave the wall openings 17. Three tips 19 and a ridge formation 51 are located on each of walls 13, 15 to facilitate the snap-fitting operation as hereinafter described.

Figure 5:
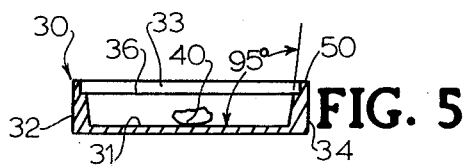
FIG. 5 is a section view taken substantially along line 5—5 of FIG. 4 and with a tissue specimen resting on the bottom of the base pan.

The second element comprising the two-part histologic tissue processing and embedding structure 10 is a base pan 30 which, like top 11, may be molded of polypropylene plastic or other suitable material having the aforementioned characteristics attributed to top 11. Base pan 30 includes a thin, heat-conducting base wall 31 and sidewalls 32, 33, 34 and 35 which, in combination with base wall 31, form the rectangular open-ended base pan 30. The exterior sidewalls 32, 33, 34, 35, as well as the exterior of top sidewalls 14, 16, are adapted to receive pencil markings for specimen identification as described later. The interior surfaces of sidewalls 32, 33, 34, 35 are provided with a continuous ledge formation 36 at a predetermined distance from base wall 31. The interior surfaces of sidewalls 32, 33, 34, 35 below ledge 36 are preferably molded so as to interconnect base wall 31 at an angle greater than 90°, as shown in FIG. 5, which allows the molded paraffin body to easily slide out of base pan 30 after hardening. An angle of 92° to 100° is a range, with 95° being preferred. Ledge 36 serves to locate top 11 at a predetermined and precise distance from base wall 31 in both the processing and embedding modes. In the preferred embodiment, the ledge 36 is located ¼ inch above the base wall 31, with ⅛ to ½ inch being an acceptable range.

The external dimensions of top 11, the formation and size of tips 19 and the internal dimensions of the open end of base pan 30 are selected in conjunction with the location of ledge 36 to provide a snap-fit between top 11 and base pan 30 for the processing mode (FIG. 1). In the embedding mode (FIG. 2) the tips 19 do not engage the interior of base sidewalls 32, 34 so that top 11 is loosely seated in the base pan 30. In one alternative embodiment, the unit 10 has been constructed so that top 11 snap-fits in base pan 30 in both the processing and embedding modes. However, it has been found that a snap-fit in the embedding mode is not necessary to facilitate clamp alignment and specimen storage since the close sliding contact between the hardened paraffin body and base sidewalls 32, 33, 34, 35 provides a firm, detachable securement between top 11 and base pan 30 once the paraffin has hardened. As described later, the loose seating of top 11 into base pan 30 in the embedding mode enables the operator to more easily mate the two members during the step of pouring molten paraffin into the unit. Top pan 11 can thus be mounted on ledge 36 in a processing mode (FIG. 1) by placing top 11 so that tips 19 firmly press against base sidewalls 32, 34 and so that top sidewalls 13, 14, 15 and 16 rest upon ledge 36 with wall 12 facing so that knobs 18 extend outwardly, or top 11 can be inverted in an embedding mode (FIG. 2) so that top 11 is loosely seated in base pan 30 and wall 12 resides on ledge 36 and knobs 18 protrude inwardly and clear of the ledge. In the processing mode, the unit 10 forms an integral, perforate enclosure having an internal distance between walls 31 and 12 of approximately 13/32 inch. In the embedding mode, wall 12 is located approximately ¼ inch from wall 31 and wall 12 is adapted to trap the hardened paraffin body.

Base wall 31 of base pan 30 has the character of being thin and in the preferred embodiment, when made of "Celcon" plastic the thickness is in the order of from 0.020 to 0.050 inch with 0.030 inch being preferable. The base wall 31 acts both to transfer heat and rapidly cool the embedded specimen as required just prior to embedding. In an alternative embodiment, the entire base pan 30 was made from stamped or pressed metal, e.g., stainless steel, in order to enhance its heat transfer characteristics.

It has been found that openings 17 in top pan 11 are adequate to allow the various fluids to enter and leave unit 10 during processing when the unit is properly positioned in the processor with perforate wall 12 and base wall 31 oriented vertically. In the preferred embodiment, about 77 openings of approximately 1 millimeter size were provided in wall 12 of top 11 and which overall was approximately 38 mm + 25 mm × 6 mm in size. In the same embodiment, base pan 30 was, overall, approximately 40 mm × 27 mm × 8 mm in size. As noted above, the proper positioning of the units 10 during processing will allow the fluids to enter and drain from the unit even without any openings in base wall 31. However, in the preferred embodiment a single aperture 38 is formed in base wall 31 to provide a drain for occasions when the unit is improperly positioned in the processor with base wall 31 facing downwardly. It should be understood that base wall 31 may be imperforate, have one aperture or have multiple apertures without departing from the scope of the invention.

In operation, a specimen identification number is penciled on the exterior surface of one of top sidewalls 14 or 16 and the same number is penciled onto one of base sidewalls 32, 33, 34, 35. This double identification procedure has proved to be the most reliable system to assure that specimens identification are not confused. During the transition from the processing mode to the embedding mode, the two members 11, 30 are separated while the specimen is oriented in base pan 30. During microtome cutting, the base pan 30 is removed. If only one of members 11, 30 were marked, the identification of the specimen could be lost if the member carrying the penciled number were mixed with other members. Thus, the double identification has proved most reliable. It is suggested that the marking on top 11 be made on either of walls 14 or 16 and the marking on base pan 30 be made on either of walls 32 or 34 so that the stored unit will reflect the identification number regardless of whether the short dimension or long dimension is exposed during storage.

With the two parts separated, a tissue specimen 40 is placed in base pan 30 (FIG. 5). The top 11 is next positioned to have its wall 12 up, as in FIG. 1, and its open end within the open end of base pan 30 so that the walls 13, 14, 15 and 16 reside on ledge 36 as also depicted in FIG. 1. A secure snap-fit is achieved by the pressure exerted by tips 19 against the interior of base sidewalls 32, 34. In this mode, it will be noticed that an enclosed perforate housing for the specimen has been formed and which will retain its integrity during handling and processing by reason of the two parts, base pan 30 and top 11, being snap-fitted and secured together. The assembled unit 10 with its specimen installed is then inserted into an automatic tissue processor with walls 12 and 31 oriented vertically and processed through fixation, dehydration, clearing and paraffin infiltration.

Figure 6:
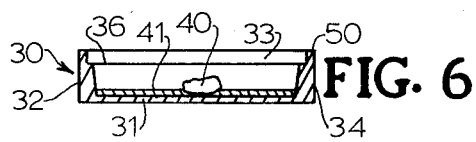
FIG. 6 is a section view like that of FIG. 5 and representing the condition of having a small amount of paraffin placed in the base pan and the tissue specimen oriented for a proper section at a later time.
Figure 7:
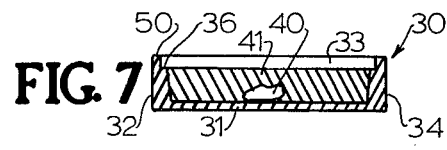
FIG. 7 is a view similar to FIGS. 5 and 6 showing the paraffin level at approximately the level of the continuous ledge formation.
Figure 8:
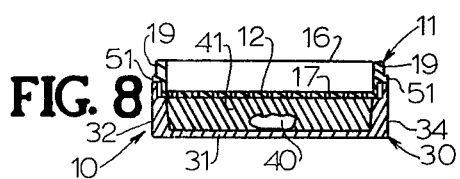
FIG. 8 is a section view taken substantially along line 8—8 of FIG. 2 with the tissue specimen partially embedded as in FIG. 7.
Figure 9:
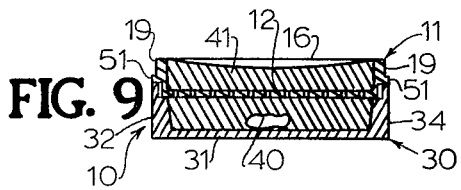
FIG. 9 is a section view like that of FIG. 8 and depicting the base pan and top member completely filled with paraffin.

Once the processing operation has been completed, top 11 is removed from base pan 30 by the lifting of one of finger-engageable ridges 51. A small amount of molten paraffin is placed in base pan 30 containing the now-processed tissue specimen 40 (FIG. 6). The bottom of base pan 30 is then cooled so that a thin layer of hardened paraffin 41 will form. As the thin layer of paraffin cools, specimen 40 thus becomes oriented in base pan 30 in a selected position. Next, molten paraffin is poured into base pan 30 to a height of approximately ¼ inch which is approximately even with ledge 36 (FIG. 7). Then top 11, with its perforated wall 12 down, is seatd into the open end of base pan 30 to form the embedding unit or mold shown in FIGS. 2 and 8. Top 11 is preferably kept warm before seating it into the base pan 30 so that a portion of the molten paraffin will not solidify when it comes in contact with top 11. Unit 10 is next completely filled with molten paraffin (FIG. 9). Wall 12 of top pan 11 in this embedding mode is resting on ledge 36. The paraffin is then allowed to harden in a cold box.

Figure 4:
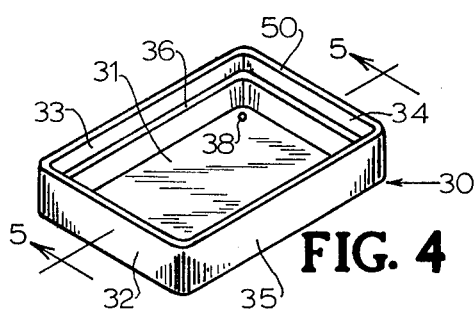
FIG. 4 is a perspective view of the base pan.
Figure 10:
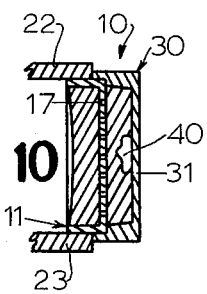
FIG. 10 is a section view of the unit clamped between the opposed jaws of a microtome clamp with the base pan lip abutting against the jaws and thereby acting as a means of aligning the embedded specimen to be sliced by the microtome cutting blade.

Preparatory to microtome cutting, walls 14, 16 of unit 10 are placed between opposing microtome jaws 22, 23 with the wall edges 50 (FIG. 4) of base pan 30 abutting against jaws 22, 23 and with top 11 residing clamped within the microtome jaws 22, 23 (FIG. 10). This procedure allows the specimen 40 and its embedding block to assume a precise position for slicing and which can be precisely repeated whenever the embedded specimen block is removed and is later returned for additional slicing. It should be noted that although the plastic walls of top 11 and base pan 30 do not form a snap-fit in the embedding mode, once the paraffin has hardened the close sliding contact between the interior of the base sidewalls 32, 33, 34, 35 and the hardened paraffin block hold the top 11 and base pan 30 securely together so that the wall edges 50 may serve the aligning function. It is, thus, important that the ledge 36 and the outer wall edges 50 (FIG. 4) be molded with precision so that base pan 30 and top 11 can always be mated together for the embedding mode in exactly the same position preparatory to slicing. This insures that the wall edges 50 of base pan 30 will, in fact, act as a precise aligning surface so that the plane of cut taken on the embedded specimen by the microtome knife in one slicing operation will be precisely parallel to a plane of cut taken later after the specimen has been stored and returned. This also means that sometimes critical specimens will not be lost in the process of trying to obtain a proper specimen alignment.

Figure 11:
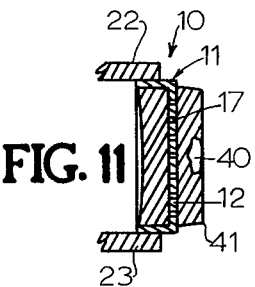
FIG. 11 is a section view like that of FIG. 10 with the base pan removed so as to prevent the tissue specimen to the blade of the microtome.
Figure 12:
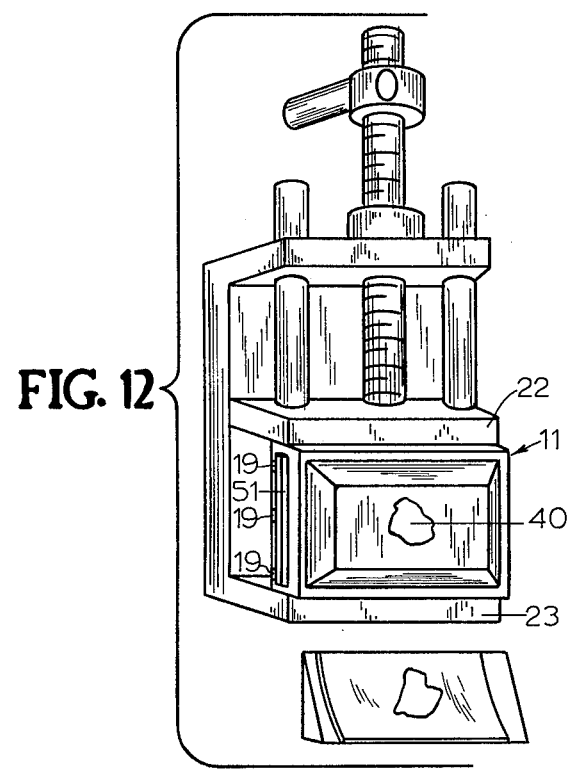
FIG. 12 is a pictorial view of the tissue specimen as it appears embedded in the exposed paraffin block and mounted for cutting by the microtome.

After the aligning procedure is complete, base pan 30 is removed from the molded paraffin unit (FIG. 11) and the necessary tissue sections are now cut on the rotary microtome (FIG. 12). After the selected number of sections have been cut, the molded unit is removed from the microtome and the open end of base pan 30 is secured to the closed end of top 11 by the aforementioned contact between sidewalls 32, 33, 34, 35 and the paraffin block so that the base pan 30 is placed over the cut paraffin block for protection of the remaining tissue specimen 40 during storage. The unit may be stored in a file with one of the penciled identification markings along either the long or short dimension exposed.

Figure 2:
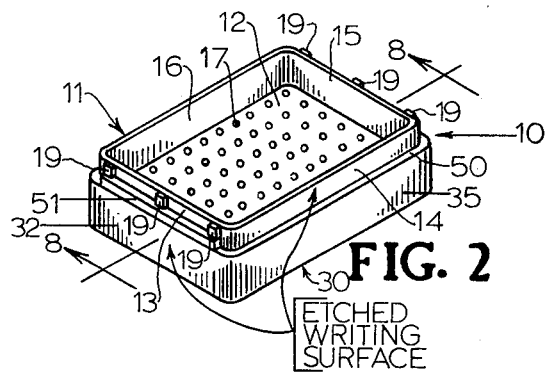
FIG. 2 is a perspective view of the base pan and top member interconnected to form an embedding unit.
Figure 3:
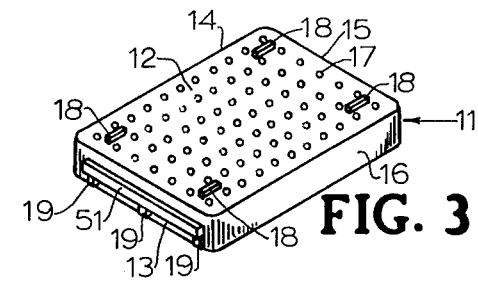
FIG. 3 is a perspective view of the top member.

What has been described is a two-part device which performs all of the functions previously performed by a minimum of three parts. To summarize, FIG. 1 depicts base pan 30 and top 11 snap-fitted together and arranged to provide an integral housing for purposes of processing and which occupies relatively little space compared to prior art receptacles. FIG. 2 depicts the same two parts in another configuration suited to providing both a mold for embedding the specimen and for securing the molded specimen to the mold itself, to providing a microtome clamp mount which can both be precisely aligned for microtome slicing and which can then hold the specimen block during slicing and finally to providing a structure suitable for protecting the embedded specimen during storage.

While many advantages are obtained by molding both base pan 30 and top pan 11 as integral structures and from a suitable plastic, it has been pointed out that other advantages could be obtained by forming top pan 11 from molded plastic and base pan 30 from stamped or pressed metal, e.g., stainless steel. When using this alternative form of the invention receptacle, the specimen after slicing and prior to storage is coated, on its cut surface, with a thin coat of paraffin for protection rather than by using a base pan 30. This alternative type of receptacle and procedure thus makes each metal base pan 30 reusable and available for use with any top 11 during processing and embedding. Only the top 11 become stored with the specimen. As and when additional slicing for the stored specimen becomes necessary, the thin coat of paraffin used during storage is simply sliced off and slicing is resumed.

It should be noted that the device of the present invention is constructed from a material which is inert to the various processing fluids, nonabsorbent and rigid. The material also has been selected so that the dimensions of the top and base pan will not change appreciably during processing and embedding, thereby assuring that the desired interconnection of the two parts is maintained at all times.

What is claimed is:

1. A composite histologic tissue structure useful for holding and transporting a tissue specimen during the processing and embedding of such specimen, for holding the embedded tissue specimen in a selected plane during microtome cutting and for storing the remaining unsliced embedded specimen, comprising in combination:
    a. a box-like top member having one end open and the opposite end closed by a central rectangular perforate wall and having interconnecting sidewalls extending from the edges of said perforated wall, said sidewalls having exterior surface means for being held between the opposing jaws of a microtome clamp during slicing of the embedded tissue specimen;
    b. a box-like base pan member having one end open and the opposite end closed by a thin, substantially flat bottom wall and having interconnecting sidewalls extending from the edges of said base wall, said base pan sidewalls having inner dimensions smaller than the outer peripheral dimensions of said top sidewalls so as to allow the top and base pan to be joined in either a processing mode wherein the open end of said top member resides within said base pan or in an embedding mode wherein the closed end of said top resides within said base pan, said base pan having ledge means formed integrally with the inner surfaces of said base pan sidewalls for supporting the edge portions of said top sidewalls remote from said perforate wall in said processing mode and for supporting the marginal edge portions of said perforate wall in said embedding mode and for locating said top member at some predetermined and precise distance from said base pan bottom wall in both said processing and embedding modes, and the inner surfaces of said base pan sidewalls between said ledge means and said bottom wall interconnecting said bottom wall at an angle greater than 90°; and
    c. cooperative means between said top and base pan for detachably securing said top to said base pan in said processing mode;

in said processing mode the composite structure providing an integral, perforate enclosure for holding and transporting the tissue specimen through the various processing fluids, and in said embedding mode the composite structure providing a mold in which said perforate wall serves to retain a hardened molded body containing the tissue specimen and formed within said base pan member.

2. The structure of claim 1 wherein when assembled in said embedding mode a pair of the outer surfaces of said top member are adapted for being grasped between the opposed jaws of a microtome clamp and the outer edges of said base pan sidewalls are adapted for being simultaneously utilized as aligning surfaces for precisely aligning said specimen in said clamp for slicing.

3. The structure of claim 1 wherein the inner surfaces of said base pan sidewalls interconnect with the bottom wall thereof at an angle between 92° and 100°.

4. The structure of claim 1 wherein the inner surfaces of said base pan sidewalls interconnect with the bottom wall thereof at an angle of approximately 95°.

5. The structure of claim 1 wherein said top member perforated wall includes a plurality of knob means extending from the outer surface thereof adapted to provide spacing in stacks of such structures during said processing.

6. The structure of claim 1 wherein said base pan bottom wall is imperforate.

7. The structure of claim 1 wherein said base pan bottom wall is provided with at least one hole for draining of fluids during processing.

8. The structure of claim 1 wherein selected outer surfaces of said members include finger engageable formation adapted to facilitate separation of said members.

9. The structure of claim 1 wherein said top member and base pan member and the respective walls thereof are each integrally formed of a molded plastic material.

10. The structure of claim 1 wherein said top member is integrally formed of a molded plastic material and said base member is integrally formed of metal.

11. The structure of claim 1 wherein said cooperative means provides for detachable securement of said top to said base pan in both the processing and embedding modes.

12. The structure of claim 1 wherein said base pan bottom wall is formed from plastic and has a thickness between 0.020 inch and 0.050 inch.

\* \* \* \* \*

UNITED STATES PATENT OFFICE
CERTIFICATE OF CORRECTION

Patent No. 3,982,862            Dated September 28, 1976

Inventor(s) John E. P. Pickett, Thomas D. Kinney, Gene M. Winders

It is certified that error appears in the above-identified patent and that said Letters Patent are hereby corrected as shown below:

In the Abstract, line 4, "sna-fitted" should be --snap-fitted--.

Col. 2, line 45, "speciments" should be --specimens--.

Col. 3, line 35, "speciment" should be --specimen--.

Col. 3, line 35, the period should be deleted after "processing".

Col. 4, line 18, "prevent" should be --present--.

Col. 5, line 64, "+" should be --x-- after 38mm.

Col. 6, line 58, "seatd" should be --seated--.

Col. 10, line 3, "formation" should be --formations--.

Signed and Sealed this

Seventeenth Day of May 1977

[SEAL]

Attest:

RUTH C. MASON  
*Attesting Officer*

C. MARSHALL DANN  
*Commissioner of Patents and Trademarks*